United States Patent [19]

Eichenberger et al.

[11] Patent Number: 5,785,720
[45] Date of Patent: Jul. 28, 1998

[54] PROCESS FOR COLORING HIGH MOLECULAR WEIGHT MATERIAL WITH POLYCYCLIC COMPOUNDS

[75] Inventors: Thomas Eichenberger, Basel; Thomas Ruch, Marly, both of Switzerland

[73] Assignee: Ciba Specialty Chemicals Corporation, Tarrytown, N.Y.

[21] Appl. No.: 709,050

[22] Filed: Sep. 6, 1996

[30] Foreign Application Priority Data

Sep. 13, 1995 [CH] Switzerland ............. 02585/95
Sep. 22, 1995 [CH] Switzerland ............. 02678/95

[51] Int. Cl.$^6$ ............. C07D 487/14; C07D 241/00; C09B 57/00; C08K 5/3462
[52] U.S. Cl. ............. 8/567; 8/636; 544/342; 544/343; 544/344; 544/346
[58] Field of Search ............. 8/567, 636; 544/342, 544/343, 344, 346

[56] References Cited

U.S. PATENT DOCUMENTS

| 4,011,086 | 3/1977 | Simson ............. 96/136 |
| 4,916,240 | 4/1990 | Kenyon ............. 549/299 |
| 5,164,496 | 11/1992 | Hochstetter ............. 540/544 |

OTHER PUBLICATIONS

Philippe, Chem. Abstract 77:48510, 1972.
Inaba et al., Chem. Abstract 75:5867, 1971.
Vertuani et al., Chem. Abstract 104:168407, 1986.
Grehn et al., Chem. Abstract 99:22185, 1983.
Tominaga et al., Chem. Abstract 80:47769, 1974.
Bailey et al., Chem. Abstract 79:142791, 1973.
Sekihachi et al., Chem. Abstract 125:278575, 1996.
Furusho et al., Synthesis and Optical resolution of axially dissymmetric pyrroles and pyrocolls: new catalysts for the enantioselective addition of diethylzinc to aromatic aldehydes, J. Chem. Soc. Perkin Trans. 1, (2), pp. 183–190, 1996.
Baraldi et al., Cosmetic preservation and structure–activity relationships of 4–diazo–pyrazole–5–carboxamides, Int. J. of Cosm. Science, 17(4), pp. 147–156, 1995.
McNab, Synthesis of pyrrolo[1,2-c]imidazol-5-one, pyrrolo[1,2-a]imidazol-5-one and pyrrolo[1,2-b]pyrazol-6-one (Three isomeric Azapyrrolizinones), by pyrolysis of Meldrum's Acid derivatives, J. Chem. Soc. Perkin Trans. 1, (3), pp. 653–656, 1987.
Schafer et al., Journal F. Prakt. Chemie., 329/4, pp. 745–748, (1987).
Sekihachi et al. Dyes & Pigments, vol. 32, No. 1, pp. 43–58, 1996, Synthesis and Chromophoric Properties of Symmetrical bis–Heteroannelated Diketopiperazines:Diimidazo–and Dipyrazolo–Piperazinediones.

Primary Examiner—Mukund J. Shah
Assistant Examiner—Deepak R. Rao
Attorney, Agent, or Firm—Kevin T. Mansfield

[57] ABSTRACT

The present invention relates to a process for bulk coloration of high molecular weight organic material, which comprises the use of a compound of the formula (I)

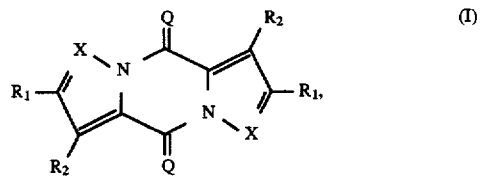

in which Q is O or S, and

X is $C(R_3)$ or N, $R_1$, $R_2$ and $R_3$ independently of one another are hydrogen, halogen chosen from the group consisting of chlorine, bromine and fluorine, $C_1$–$C_6$alkyl, $C_1$–$C_6$alkoxy, hydroxyl, cyano, nitro, amino, morpholino,

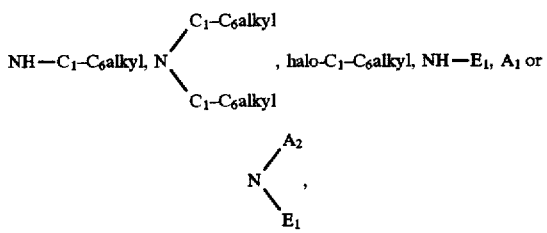

in which $A_1$ and $A_2$ independently of one another are unsubstituted or substituted $C_6$–$C_{12}$aryl or $C_3$–$C_{12}$heteroaryl, which contains, in the ring system, 1 to 3 hetero atoms chosen from the group consisting of N, O and S, and $E_1$ is

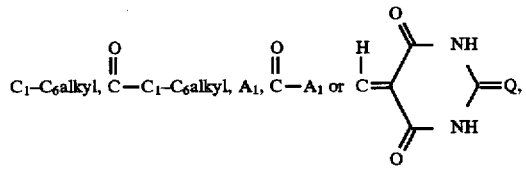

or $R_1$ and $R_2$ together, or $R_1$ and $R_3$ together, are a radical $A_3$, which $A_3$ is unsubstituted or substituted $C_4$–$C_8$alkenylene or $C_8$–$C_{12}$arylene.

Individual novel compounds of the formula (I) are claimed themselves.

15 Claims, No Drawings

PROCESS FOR COLORING HIGH MOLECULAR WEIGHT MATERIAL WITH POLYCYCLIC COMPOUNDS

The invention relates to colouring polymers with certain polycyclic compounds, novel compositions of substances comprising these compounds, and individual polycyclic compounds of this group themselves.

Pigments which are suitable for wide use in polymers are in general subject to the following requirements: high purity of the colour shade (saturation), high tinctorial strength and high fastness properties, for example stability to light or heat. Although the yellow pigments customary nowadays meet individual requirements of this list, they still do not have all the desired properties.

As a rule, only those pigments of which the molecules themselves have a high chemical stability and undergo reactions only under drastic conditions have good properties. It has now been found that certain polycyclic compounds which can easily be hydrolysed because of their chemical structure surprisingly have excellent properties as colourants.

The present invention thus relates to a process for bulk coloration of high molecular weight organic material, which comprises the use of a compound of the formula (I)

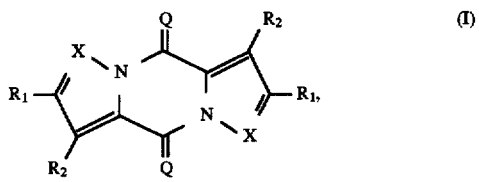

in which Q is C or S, and
X is C($R_3$) or N,
$R_1$, $R_2$ and $R_3$ independently of one another are hydrogen, halogen chosen from the group consisting of chlorine, bromine and fluorine, $C_1$–$C_6$alkyl, $C_1$–$C_6$alkoxy, hydroxyl, cyano, nitro, amino, morpholino,

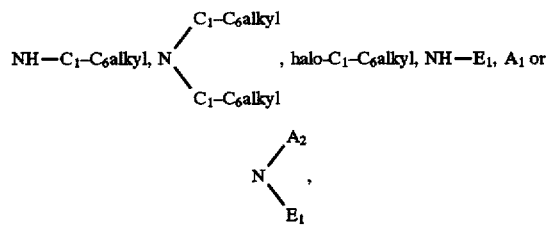

in which $A_1$ and $A_2$ independently of one another are $C_6$–$C_{12}$aryl substituted by 3 radicals $R_4$, $R_5$ and $R_6$, or $C_3$–$C_{12}$heteroaryl which is substituted by 3 radicals $R_4$, $R_5$ and
$R_6$ and contains, in the ring system, 1 to 3 hetero atoms chosen from the group consisting of N, O and S, and $E_1$ is

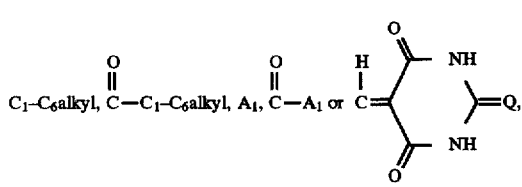

or $R_1$ and $R_2$ together, or $R_1$ and $R_3$ together, are a radical $A_3$, which $A_3$ is $C_4$–$C_8$alkenylene or $C_8$–$C_{12}$aralkenylene which are substituted by 3 radicals $R_7$, $R_8$ and $R_9$,
and $R_4$ to $R_9$ independently of one another are hydrogen, halogen chosen from the group consisting of chlorine, bromine and fluorine, $C_1$–$C_6$alkyl, $C_1$–$C_6$alkoxy, hydroxyl, cyano, nitro, amino, morpholino,

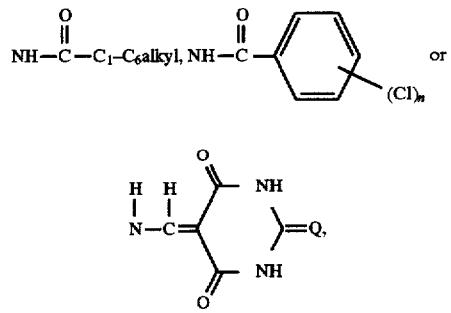

in which n is zero or an integer from 1 to 3.

In some cases, formula (I) and the formulae given below represent only one of the possible tautomeric structures to which, however, the present invention may also extend. The compounds of the formula (I) and tautomers thereof are yellow pigments which meet the abovementioned requirements to a high degree.

$C_6$–$C_{12}$aryl is isocyclic aromatic radicals, for example phenyl, 4-biphenylyl, 1-naphthyl or 2-naphthyl.

$C_3$–$C_{12}$heteroaryl is polyunsaturated heterocyclic radicals, for example pyridyl, quinolyl, isoquinolyl, bipyridyl, triazinyl, furyl, benzofuryl, dibenzofuryl, pyrrolyl, thienyl, furfuryl, isothiazolyl, naphthyridinyl, quinoxalinyl, imidazolyl, oxazolyl, pyrazolyl, pyrazinyl, pyrimidinyl, phenothiazinyl, benzotriazolyl, benzoxazolyl or carbazolyl, preferably mono- and bicyclic heteroaromatic radicals.

$C_4$–$C_8$alkenylene is a polyunsaturated linear or branched radical, for example 1,4-buta-1,3-dienylene or 2,5-hexa-2,4-dienylene.

$C_8$–$C_{12}$aralkenylene is polyunsaturated radicals having an aromatic character which contain at least one ring, for example

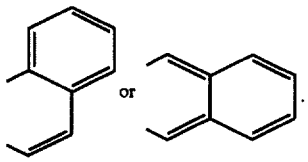

Halo-$C_1$–$C_6$alkyl is $C_1$–$C_6$alkyl, some or all of the hydrogen atoms of which are replaced by halogen atoms, such as bromine, chlorine or fluorine. Examples of halo-$C_1$–$C_6$alkyl are, in particular, trichloromethyl, fluoromethyl, trifluoromethyl, pentafluoroethyl, β,β,β-trifluoroethyl, ω-chloropropyl, ω-bromobutyl or perfluorohexyl.

The following compounds of the formula (I) listed as examples illustrate the invention in a particularly descriptive manner without thereby limiting the invention in any way:

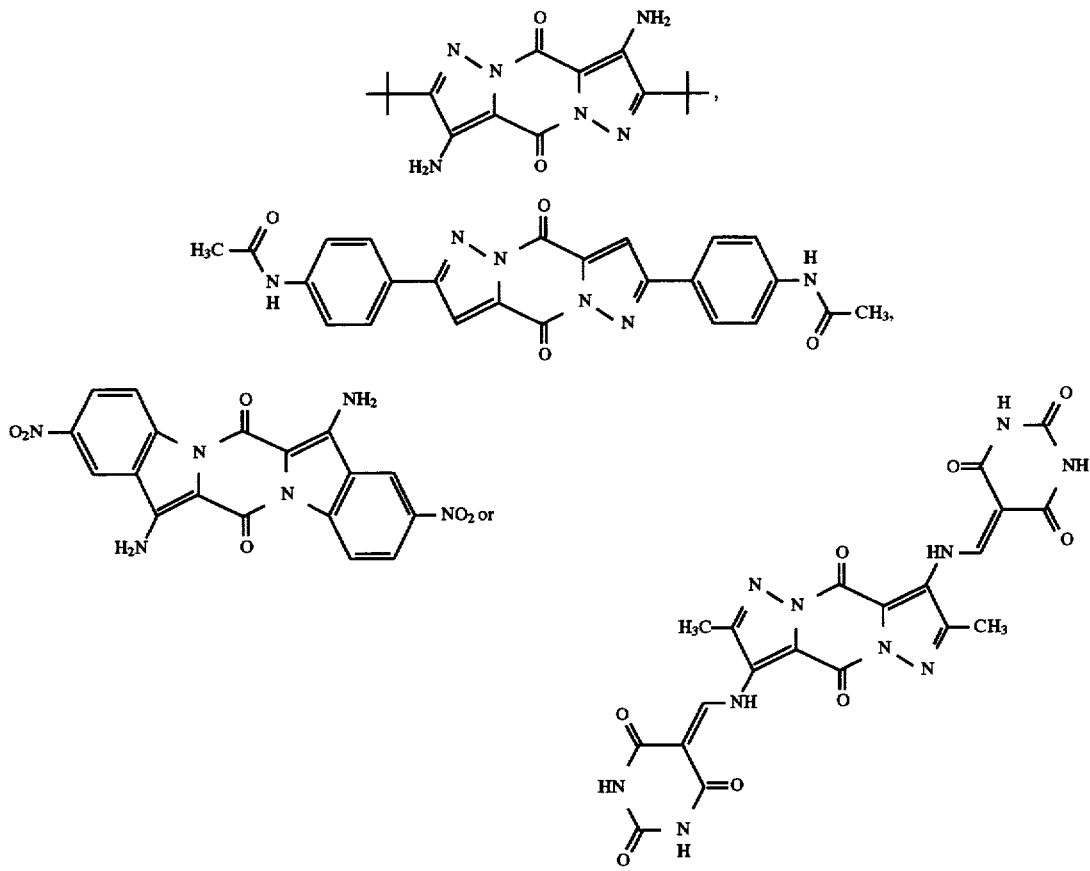

In

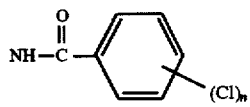

n is preferably zero or the integer 1 or 2, particularly preferably zero, and, where appropriate, the chlorine substituents are particularly preferably in the o-, p- or o,p-position relative to the amide group.

Q is preferably O.

If X is N, $R_1$ and $R_2$ are preferably $C_1$–$C_4$alkyl, $C_1$–$C_4$alkoxy, amino, $A_4$, NH—$A_4$ or NH—$E_1$, which $A_4$ is a radical $A_1$, particularly preferably $C_6$–$C_{12}$aryl, substituted by 3 radicals $R_{10}$, $R_{11}$ and $R_{12}$, in which $R_{10}$ to $R_{12}$ independently of one another are $R_4$ to $R_6$, particularly preferably hydrogen, $C_1$–$C_6$alkoxy, amino,

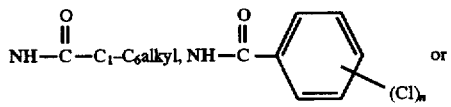

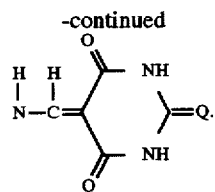

If X is C($R_3$), one radical $R_1$ or $R_2$ is preferably $C_1$–$C_4$alkyl, $C_1$–$C_4$alkoxy, amino, $A_4$, NH—$A_4$ or NH—$E_1$, and $R_1$, together with the other particular radical $R_2$ or, in particular, $R_3$, preferably forms a radical

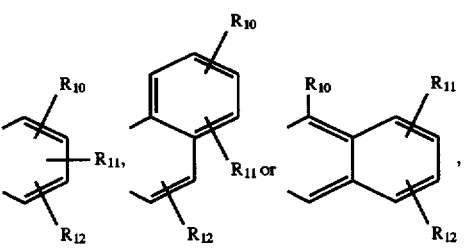

in which $A_4$, $E_1$ and $R_{10}$ to $R_{12}$ are as defined above.

The use of the compounds of the formula (I) wherein

1] X is N, $R_1$ is methyl, ethyl or $A_4$ and $R_2$ is amino or NH—$E_1$, in which $A_4$ and $E_1$ are as defined above;

2] X is N, $R_1$ is a radical $A_4$ and $R_2$ is hydrogen, in which $A_4$ is as defined above;

3] X is N, $R_1$ is hydrogen and $R_2$ is amino, morpholino,

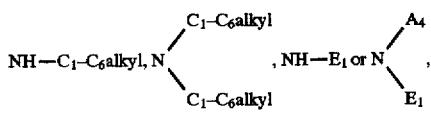

in which $A_4$ and $E_1$ are as defined above; or

4] X is $C(R_{13})$, $R_1$ and $R_2$ together are a radical

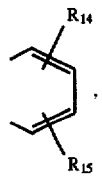

is amino or NH—$E_1$ and $R_{14}$ and $R_{15}$ independently of one another are hydrogen, amino, NH—$E_1$ or nitro, in which $E_1$ is as defined above, is particularly preferred.

The use of the compounds of the formula (I) which contain at least two hydrogens each bonded to a nitrogen in at least one tautomeric form is especially preferred.

Most of the compounds of the formula (I) are known and can be prepared by known methods. For example, a compound of the formula (II)

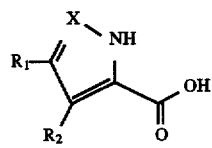
(II)

can be cyclodimerized with dicyclohexylcarbodiimide and pyridine, water being split off, as described in DE-4102921, or a compound of the formula (III),

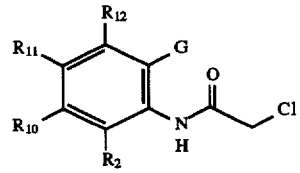
(III)

in which G is, for example, CN, CO—$C_1$–$C_6$alkyl, CO—$A_1$ or CO—O—$C_1$–$C_6$alkyl, can be cyclized by the "Thorpe-Ziegler" method, as described by H. Schäfer and K. Gewald in Journal für praktische Chemie 329/4, 745–748 (1987).

Compounds of the formula (I) which are still not known can be prepared, where appropriate, from known substances by known methods, or closely analogously thereto. It is also possible to convert compounds of the formula (I) into other compounds of the formula (I) by known methods.

The choice of the most suitable method depends on the nature of the substituents.

Such modifications in functionality are trivial and well known to any expert. A quick overview of which groups can be converted into which other groups is given, for example, in the series "Compendium of Organic Synthetic Methods" (John Wiley & Sons, from 1971).

In the case of such modifications in the substituents without conversion of the polycyclic skeleton it is preferable to start from a compound which is at least partly soluble and to convert it into a compound of the formula (I) having pigment properties.

The groups Q can also be modified subsequently. For example, oxo can be converted into thioxo by treatment with tetraphosphorus decasulfide, whereupon compounds of the formula (I) in which Q is S can be obtained.

The compounds of the formula (I) also include some which are novel.

The present invention accordingly also relates to a compound of the formula (IV), (V) or (VI),

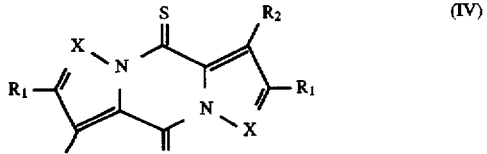
(IV)

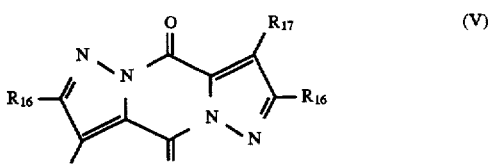
(V)

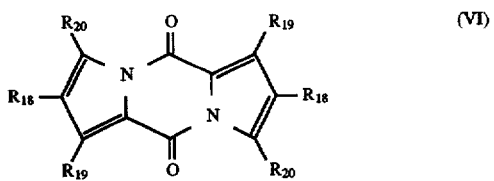
(VI)

wherein X, $R_1$ and $R_2$ are as defined above in formula (I);

$R_{16}$ and $R_{17}$ independently of one another are hydrogen, halogen chosen from the group consisting of chlorine, bromine and fluorine, $C_1$–$C_6$alkyl, $C_1$–$C_1$alkoxy, hydroxyl, cyano, nitro, amino, morpholino,

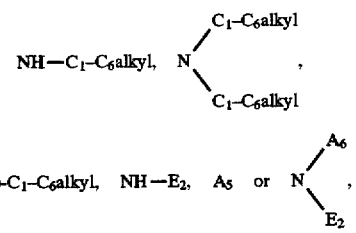

in which $A_5$ and $A_6$ independently of one another are $C_6$–$C_{12}$aryl substituted by 3 radicals $R_{21}$, $R_{22}$ and $R_{23}$, or $C_3$–$C_{12}$heteroaryl which is substituted by 3 radicals $R_{21}$, $R_{22}$ and $R_{23}$ and contains, in the ring system, 1 to 3 hetero atoms chosen from the group consisting of N, O and S, and

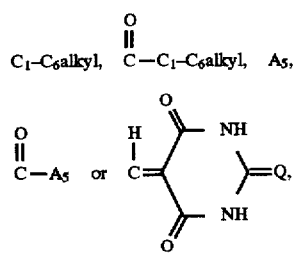

with the proviso that either $R_{16}$ is $C_6$–$C_{12}$aryl substituted by at least one radical of the group consisting of $C_1$–$C_6$alkoxy, amino, morpholino,

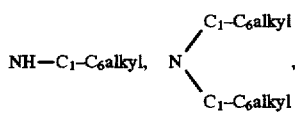

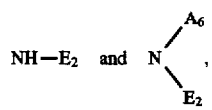

or $R_{17}$ is $C_1$–$C_6$alkoxy, amino, morpholino,

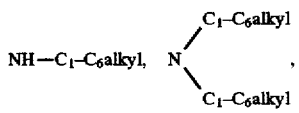

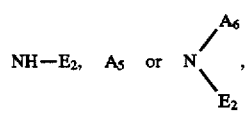

or $R_{16}$ and $R_{17}$ together are a radical $A_7$, in which $A_7$ is $C_4$–$C_8$alkenylene or $C_8$–$C_{12}$arylene which are substituted by 3 radicals $R_{24}$, $R_{25}$ and $R_{26}$, with the proviso that $A_7$ is substituted by at least one radical $C_1$–$C_6$alkoxy;

$R_{18}$, $R_{19}$ and $R_{20}$ independently of one another are hydrogen, halogen chosen from the group consisting of chlorine, bromine and fluorine, $C_1$–$C_6$alkyl, $C_1$–$C_6$alkoxy, hydroxyl, cyano, nitro, amino, morpholino,

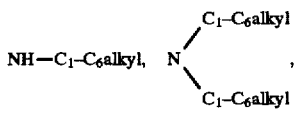

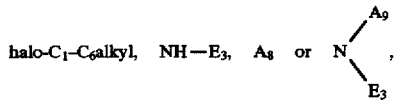

in which $A_8$ and $A_9$ independently of one another are $C_6$–$C_{12}$aryl substituted by 3 radicals $R_{21}$, $R_{22}$ and $R_{23}$, or $C_3$–$C_{12}$heteroaryl which is substituted by 3 radicals $R_{21}$, $R_{22}$ and $R_{23}$ and contains, in the ring system, 1 to 3 hetero atoms chosen from the group consisting of N, O and S, and $E_3$

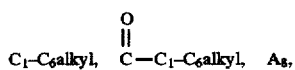

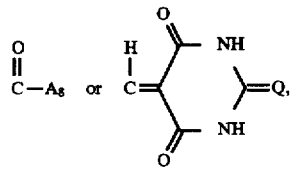

with the proviso that either $R_{19}$ is $C_1$–$C_6$alkoxy, amino, morpholino,

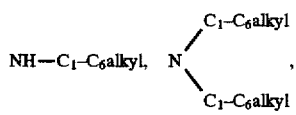

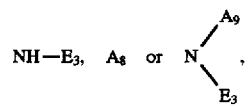

if $R_{20}$ is a radical $A_8$, is at least one substituent $R_{21}$, or $R_{18}$ is $C_1$–$C_6$alkoxy, amino, morpholino,

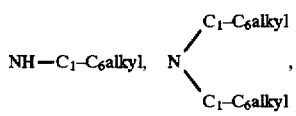

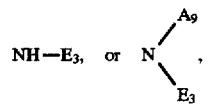

or $R_{18}$ and $R_{19}$ together are a radical $A_{10}$, which $A_{10}$ is $C_4$–$C_8$alkenylene or $C_8$–$C_{12}$arylene substituted by 3 radicals $R_{24}$, $R_{25}$ and $R_{26}$, with the proviso that $A_{10}$ is substituted by at least one radical from the group consisting of $C_1$–$C_6$alkoxy, amino, morpholino,

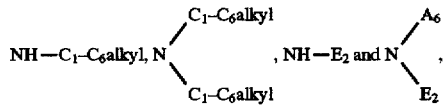

or $R_{18}$ and $R_{20}$ together are a radical $A_{11}$, which $A_{11}$ is $C_4$–$C_8$alkenylene or $C_8$–$C_{12}$arylene which are substituted by 3 radicals $R_{24}$, $R_{25}$ and $R_{26}$, with the proviso that, if $R_{18}$ and $R_{20}$ together are a radical $A_{11}$, $R_{19}$ is other than hydrogen, and, if $R_{19}$ is amino or $C_1$–$C_6$alkyl, $A_{11}$ is substituted by at least one radical from the group consisting of $C_1$–$C_6$alkoxy, amino, morpholino,

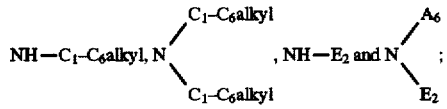

in which $R_{21}$ to $R_{26}$ independently of one another are hydrogen, halogen chosen from the group consisting of chlorine, bromine and fluorine, $C_1$–$C_6$alkyl, $C_1$–$C_6$alkoxy, hydroxyl, cyano, nitro, amino, morpholino,

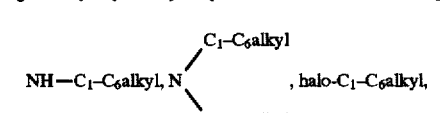

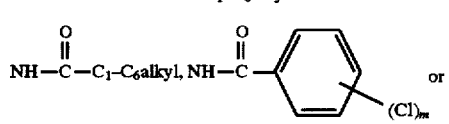

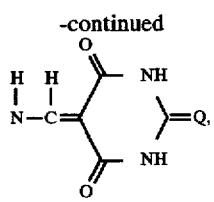

in which m is zero or an integer from 1 to 3; and Q is O or S.

The compounds of the formulae (IV), (V) and (VI) are suitable as colourants. Those compounds of the formulae (IV), (V) and (VI) which contain at least one group from the series consisting of $C_1$–$C_6$alkoxy, amino, morpholino,

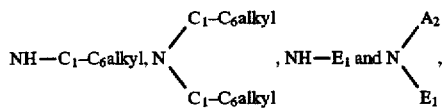

in which $A_1$, $A_2$ and $E_1$ are as defined in the case of formula (I), are preferred.

Depending on the nature of their substituents and of the polymer to be coloured, the compounds of the formulae (I), (IV), (V) and (VI) can be used as polymer-soluble dyes or, in particular, as pigments. In the latter case, it is advantageous to convert the products obtained in the synthesis into a finely dispersed form. This can be done in various ways, for example:

a] by grinding or kneading, advantageously in the presence of grinding auxiliaries, such as inorganic or organic salts, with or without the addition of organic solvents; after the grinding, the auxiliaries are removed in the customary manner, for example soluble inorganic salts by washing with water and water-insoluble organic solvents by steam distillation.

b] by reprecipitation on from sulfuric acid, methanesulfonic acid, trichloroacetic acid or polyphosphoric acid.

It may prove to be advantageous for the crude pigments or the pigments treated according to a] or b] to be after-treated with organic solvents, preferably with those which have boiling points above 100° C. This treatment usually lasts from ¼ to 72 hours, and if appropriate can be carried out at elevated temperature , for example at 30° to 200° C.

Solvents which prove to be particularly suitable are benzenes substituted by halogen atoms or alkyl or nitro groups, such as xylenes, chlorobenzene, o-dichlorobenzene or nitrobenzene, and pyrdine bases, such as pyridine, picoline or quinoline, and furthermore ketones, such as cyclohexanone, ethers, such as ethylene glycol monomethyl or monoethyl ether, amides, such as dimethylformamide or N-methylpyrrolidone, and dimethyl sulfoxide, sulfolane or water by itself, if appropriate under pressure. The after-treatment can also be carried out in water in the presence of organic solvents and/or with the addition of surface-active substances.

The pigments preferably have a BET surface area [determined in accordance with DIN 66132, *Determination of the specific surface area of solids by nitrogen adsorption/ 1.- Differential method according to Haul and Dümbgen* (July 1975 edition)] of 5–150 $m^2/g$. Pigments which have a BET surface area of 5–30 $m^2/g$ have rather an opaque character, while those having BET surface areas of 30–150 $m^2/g$ are rather transparent. The BET surface area and the particle size distribution can be controlled by the above-mentioned after-treatments.

Depending on the intended use, it proves advantageous to use the pigments as toners or in the form of preparations. Depending on the conditioning process or intended use, it may be advantageous to add to the pigment certain amounts of texture-improving agents before or after the conditioning process if these have no adverse effect when the pigments are used for colouring high molecular weight organic materials, in particular polyethylene. Texture-improving agents are, in particular, fatty acids having at least 18 C atoms, for example stearic or behenic acid, or amides or metal salts thereof, in particular Mg salts, as well as plasticizers, waxes, resin acids, such as abietic acid, colophony soap, alkylphenols or aliphatic alcohols, such as stearyl alcohol, or aliphatic 1,2-dihydroxy compounds having 8 to 22 C atoms, such as 1,2-dodecanediol, and furthermore modified colophony-maleate resins or fumaric acid-colophony resins. The texture-improving agents are preferably added in amounts of 0.1 to 30% by weight, in particular 2 to 15% by weight, based on the end product. The abovementioned 1,2-dihydroxy compounds, in particular 1,2-dodecanediol, can also be employed for improving filtration of the suspended pigment composition.

The compound of the formula (I) can be employed in an amount of 0.01 to 30% by weight, preferably 0.1 to 10% by weight, based on the high molecular weight organic material to be coloured.

The invention therefore also relates to compositions of substances comprising a compound of the formula (I) and a high molecular weight organic material.

The compositions of substances which are of particular interest or preferred are those which comprise a compound of the formula (I) which is used in the processes for dyeing high molecular weight organic material which are defined above as of particular interest or preferred.

The compounds of the formula (I) can be used individually for colouring organic materials. However, it is also possible to employ several compounds of the formula (I) simultaneously as mixtures, or to use so-called solid solutions or mixed crystals in which one compound of the formula (I) and another compound of the formula (I), or a compound of the formula (I) and a colourant of another chemical class are embedded together.

The high molecular weight organic material to be coloured according to the invention can be of natural or synthetic origin. The material can be, for example, natural resins or drying oils, rubber or casein, or modified natural substances, such as chlorinated rubber, oil-modified alkyd resins, viscose, cellulose ethers or esters, such as ethylcellulose, cellulose acetate, cellulose propionate or cellulose acetobutyrate, or nitrocellulose, but in particular fully synthetic organic polymers (thermosetting resins and thermoplastics) such as are obtained by polymerization, polycondensation or polyaddition. Materials from the class of polymerization resins are primarily polyolefins, such as polyethylene, polypropylene or polyisobutylene, and furthermore substituted polyolefins, such as polymers of vinyl chloride, vinyl acetate, styrene, acrylonitrile or acrylic acid esters and/or methacrylic acid esters, or butadiene, as well as copolymers of the monomers mentioned, in particular ABS or EVA.

Polyaddition resins and polycondensation resins include the condensation products of formaldehyde with phenols, the so-called phenoplasts, and the condensation products of formaldehyde with urea, thiourea and melamine, the so-called aminoplasts, the polyesters used as surface coating resins, both saturated, for example alkyd resins, and unsaturated, for example maleate resins, and furthermore the linear polyesters and polyamides, polyurethanes or silicones.

The high molecular weight compounds mentioned can be present individually or as mixtures, as plastic compositions or melts, which can be spun to fibres if appropriate.

They can also be in the form of their monomers or in the polymerized state in dissolved form as film-forming agents or binders for paints or printing inks, for example linseed oil varnish, nitrocellulose, alkyd resins, melamine resins and urea-formaldehyde resins or acrylic resins.

The high molecular weight organic substances are pigmented with the pigments of the formula (I), for example, by admixing such a pigment, if appropriate in the form of masterbatches, to these substrates using roll mills or mixing or grinding apparatus. The pigmented material is then brought into the desired final form by processes known per se, such as calendering, compression moulding, extrusion, brushing, casting or by injection moulding. For production of non-rigid mouldings or in order to reduce their brittleness, it is often desirable to incorporate into the high molecular weight compounds so-called plasticizers before shaping. Plasticizers which can be used are, for example, esters of phosphoric acid, phthalic acid or sebacic acid. In the process according to the invention, the plasticizers can be incorporated into the polymers before or after incorporation of the pigment dye. For the purpose of achieving different colour shades, it is furthermore possible also to add fillers or other colouring constituents, such as white, coloured or black pigments, to the high molecular weight organic substances in any amounts, in addition to the compounds of the formula (I).

For pigmenting paints and printing inks, the high molecular weight organic materials and the compounds of the formula (I) are finely dispersed or dissolved in a common organic solvent or solvent mixture, if appropriate together with additives such as fillers, other pigments, siccatives or plasticizers. A procedure can be followed here in which the individual components by themselves, or else several of them together, are dispersed or dissolved and only then are all the components brought together.

The resulting colorations, for example in plastics, fibres, paints or prints, are distinguished by a yellow to orange-red colour shade, a very high tinctorial strength, high saturation, good dispersibility, good fastness to overspraying, migration, heat, light and weathering and a high gloss and good IR reflectance properties. The yellow pigments according to the invention are of particular interest as a result of their neutral yellow colour shade in combination with a high tinctorial strength, saturation and good fastnesses.

If the high molecular weight material to be coloured is a paint, it can be a usual paint or else a special paint, for example an automotive finish, preferably a metallic finish comprising metal or mica particles, for example.

The compounds of the formula (I) can also be used as photoelectrophoretic toners.

If the compounds of the formula (a) are present as a solution in the polymers used, they are also distinguished by a pure colour shade, high tinctorial strength, high fastness to light and furthermore by a high fluorescence. They are suitable in solar energy collectors and for the production of laser beams.

The following examples illustrate the invention:

EXAMPLE 1

11.8 g of the compound of the formula (VII)

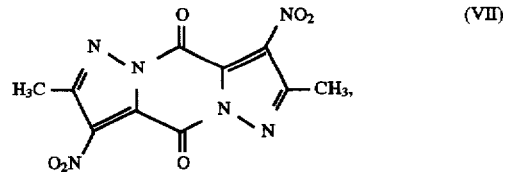

(prepared according to Beilstein E III/IV 26, 2508) are suspended in 120 ml of dimethylformamide (DMF) and hydrogenated with hydrogen under normal pressure at 50° C., with the addition of 1.2 g of palladium/active charcoal (10% by weight). After 6 hours, a further 1.2 g of palladium/active charcoal and 60 ml of DMF are added. After a further 19 hours, 1.2 g of palladium/active charcoal are again added and the reaction mixture is stirred for a further 15 hours, during which the reaction stops. The total consumption of hydrogen is 4.561 (88% of theory). The green-yellow suspension is diluted with 1 l of DMF, heated to 130° C. and stirred for a further 30 minutes, and filtered through a hard paper filter. After the residue has been washed with 400 ml of DMF, the filtrate is concentrated to about 200 ml and the concentrate is then left to stand at room temperature for 16 hours and filtered. The residue is washed with 200 ml of methanol. 2.86 g (30% of theory) of an orange-coloured powder of the formula (VIII)

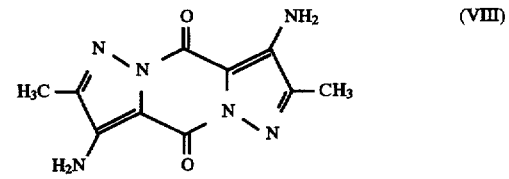

and the elemental composition: 48.73% C, 4.22% H, 33.42% N;

(calculated for $C_{10}H_{10}N_6O_2$: 48.78% C, 4.09% H, 24.13% N)

are obtained.

EXAMPLE 2

2.46 g of the compound of the formula (VIII) from Example 1 and 2.58 g of barbituric acid are suspended in 80 ml of DMF. 5 ml of triethyl orthoformate are stirred into the orange suspension; the reaction mixture is heated up to 130° C., during which the ethanol liberated in the reaction is distilled off. The now yellow suspension is stirred at 130° C. for a further 21 hours and filtered and the residue is washed with 100 ml of DMF, 300 ml of methanol and 300 ml of water. The still somewhat moist press-cake is taken up in 90 ml of dimethylacetamide and the mixture is stirred at 130° C. for 6 hours. The suspension is cooled to room temperature and filtered off and the residue is washed with 200 ml of methanol and 200 ml of water and dried. 3.73 g (71% of theory) of orange-coloured powder of the formula (IX)

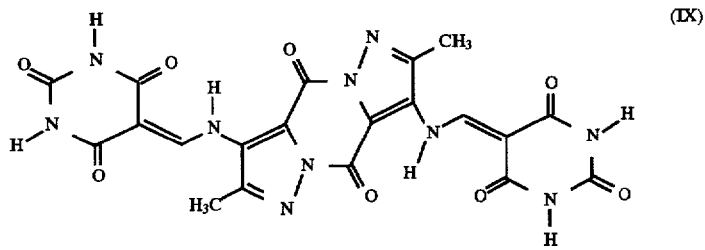

(IX)

and the elemental composition: 45.10% C, 3.45% H, 26.16% N (calculated for $C_{20}H_{14}N_{10}O_8 \cdot 0.6\ H_2O$: 45.05% C, 2.87% H, 26.27% N) are obtained.

EXAMPLE 3

1.29 g of the compound of the formula (X),

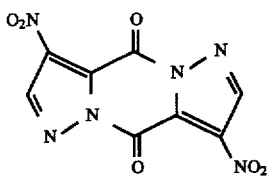

(X)

prepared according to Baraldi et al., Int. J. Cosmet. Sci. 1995/17, 147–56, are hydrogenated in 200 ml of DMF with 0.5 g of 5% Pd on active charcoal at 25°–35°C. under a pressure of 15 bar. After 20 hours, the reaction has ended, the uptake of hydrogen being 0.62 l (100% of theory). The reaction mixture is filtered over a hard paper filter and washed with 100 ml of DMF heated to 60° C. The intensely yellow-brown filtrate is concentrated to a volume of about 5 ml on a Rotavapor and the concentrate is left to stand at 0°–5° C., for 2 days. The yellow-brown, very fine crystals which have precipitated out are filtered off, washed with 10 ml of methanol and dissolved in 60 ml of hot DMF. After the solution has been concentrated to about 5 ml and the concentrate has been left to stand at room temperature for 4 hours, the concentrate is filtered and the residue is dried: 105 mg (10% of theory) of ochre-coloured powder of the formula (XI)

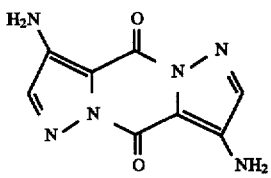

(XI)

and the elemental composition: 42.65% C, 3.01% H, 37.30% N (calculated for $C_8H_6N_6O_2 \cdot 0.4\ H_2O$: 42.63% C, 3.04% H, 37.29% N)

are obtained.

EXAMPLE 4

25.64 g of the compound of the formula (XII),

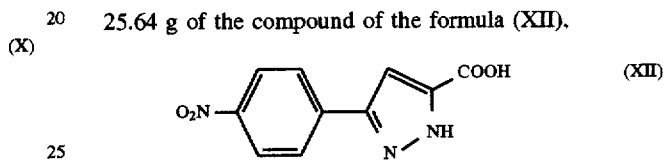

(XII)

prepared according to Beilstein E III/IV 25, page 841, are stirred under reflux in 130 ml of thionyl chloride for 17 hours. Thereafter, about 80% of the thionyl chloride is distilled off and 100 ml of toluene are added. The reaction mixture is filtered and the residue is washed with 240 ml of acetone and 300 ml of water and dried; 10.07 g (43% of theory) of a pale brown powder of the formula (XIII)

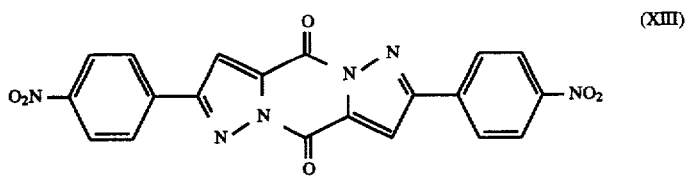

(XIII)

and the elemental composition: 55.58% C, 2.43% H, 19.66% N (calculated for $C_{20}H_{10}N_6O_6$: 55.82% C, 2.34% H, 19.53% N)

are obtained.

10.07 g of the compound of the formula (XIII) thus prepared are hydrogenated in 500 ml of DMF with the addition of 1.0 g of 5% Pd on active charcoal at room temperature and under normal pressure. After 18 hours, the reaction has ended, the uptake of hydrogen being 3.05 l (97% of theory). The reaction mixture is filtered over a hard paper filter and washed with 100 ml of DMF (if the hydrogenated compound has already precipitated out in the reaction mixture, the mixture must first be diluted with further DMF and heated up before the filtration).

The red-brown filtrate is concentrated to about 50 ml and the concentrate is stirred into 2 l of water in the course of 30 minutes. The red-brown precipitate is filtered off, washed with 300 ml of water and dried; 7.84 g (91% of theory) of a red-brown powder of the formula (XIV)

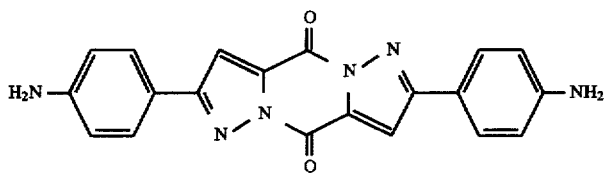

(XIV)

and the elemental composition: C 63.50%, H 3.92%, N 22.33%

(calculated for $C_{20}H_{14}N_6O_2 \cdot 0.4\ H_2O$: C 63.62%, H 3.95%, N 22.26%)

are obtained.

1.23 g of the compound of the formula (XIV) prepared above are suspended in 60 ml of N-methylpyrrolidone (NMP). 10 ml of acetic anhydride are added and the reaction mixture is heated up continuously to 155° C. in the course of 30 minutes, during which the colour of the suspension changes from red-brown to dark yellow. Stirring is now continued for a further 45 minutes, without heating, the reaction mixture, which is still hot at 75° C., is filtered over a hard filter paper and the residue is washed with 20 ml of NMP and 20 ml of methanol. The crude product thus obtained is recrystallized in 40 ml of boiling dimethylacetamide (DMA) for one hour and the product is filtered off over a hard paper filter and washed with 20 ml of ethanol. After drying, 960 mg (78% of theory) of a yellow powder of the formula (XV)

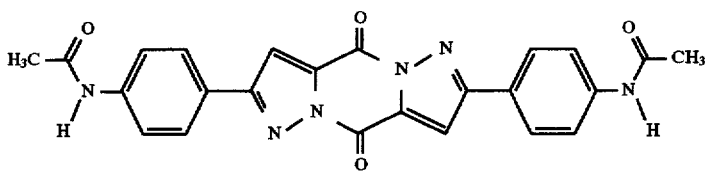

(XV)

and the elemental composition: C 61.07%, H 5.62%, N 17.70%

(calculated for $C_{24}H_{18}N_6O_4 \cdot H_2O$: C 61.01%, H 4.26%, N 17.79%)

are obtained.

The molecular weight of 454 calculated for the composition $C_{24}H_{18}N_6O_4$ was additionally confirmed by a mass spectrogram (DEI).

EXAMPLE 5

11.98 g of the compound of the formula (XVI),

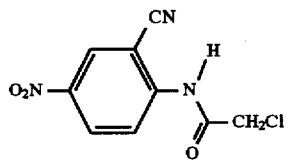

(XVI)

prepared according to K. Gewald et al, Chem. Ber. 124, 1237–41 (1991), are suspended in 40 ml of anhydrous diethylene glycol dimethyl ether (diglyme), 3.44 g of sodium tert-amylate (content: 80%) are added and the reaction mixture is heated up to 85° C. It is stirred at 85° C. for 6 hours and then for a further hour without heating. The reaction mixture is filtered, the red-brown residue is washed with 200 ml of water and suspended in 80 ml of 100% acetic acid while still moist, and the suspension is stirred at room temperature for 30 minutes. It is filtered and the residue is washed with 200 ml of water and dried. 3.1 g (31% of theory) of a red-brown powder of the formula (XVII)

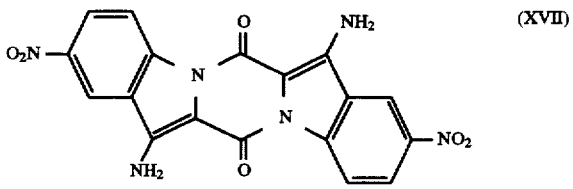

(XVII)

and the elemental composition: C 52.29%, H 2.71 %, N 20.24%

(calculated for $C_{18}H_{10}N_6O_6 \cdot 0.4\ H_2O$: C 52.28%, H 2.63%, N 20.32%)

are obtained.

EXAMPLE 6

30.82 g of 2-amino-4-chlorobenzonitrile are suspended in 450 ml of anhydrous toluene, and 24.2 ml of chloroacetyl chloride are added. The reaction mixture is cooled to −5° C. and 49 ml of dry triethylamine are added in the course of 4 hours. Stirring is continued at room temperature without cooling for a further 18 hours and the reaction solution is poured into 2 l of acetic acid ethyl ester (ethyl acetate). The mixture is extracted by shaking 3> with 700 ml of water each time, the organic phase is dried with anhydrous sodium sulfate and this solution is purified over a column containing 100 g of silica gel (rinsing with 500 ml of ethyl acetate). The solution is concentrated to dryness, the residue is suspended in 150 ml of methanol, the suspension is filtered and the residue is washed with 600 ml of petroleum ether. After drying, 31.36 g (68% of theory) of a pale beige powder of the formula (XVIII)

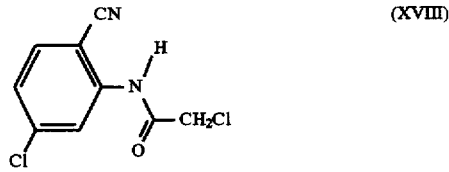

(XVIII)

and the elemental composition: C 47.12%, H 2.71%, N 12.22%, Cl 30.78%

(calculated for $C_9H_6N_2OCl_2$: C 47.19%, H 2.64%, N 12.23%, Cl 30.95%)

which melts at 161° C, are obtained.

9.16 g of the compound of the formula (XVIII) described above are suspended in 40 ml of anhydrous diglyme, 2.75 g of sodium tert-butylate (content: 80%) are added and the mixture is heated at 65° C. for 4 hours. It is allowed to cool to room temperature in the course of one hour, 5 ml of 100% acetic acid are added and the mixture is subsequently stirred at room temperature for a further 17 hours. The yellow suspension is filtered off and the residue is washed with 200 ml of acetic acid and 400 ml of water. The crude product is recrystallized in 50 ml of DMA for 2 hours and the crystals are filtered off, washed with 160 ml of methanol and 200 ml of water and dried; 4.41 g of a yellow powder of the formula (XIX)

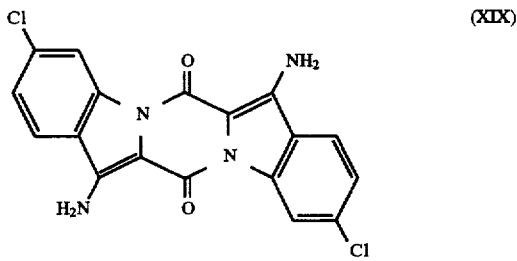

(XIX)

and the elemental composition: C 55.85%, H 2.75%, N 14.52%, Cl 18.26%

(calculated for $C_{18}H_{10}N_4O_2Cl_2$: C 56.12%, H 2.62%, N 14.54%, Cl 18.41%)

are obtained.

2.3 g of the compound of the formula (XIX) described above are heated at 120° C. together with 1.8 ml of acetyl chloride in 100 ml of dimethylacetamide for 20 hours. The pale yellow suspension is stirred for a further hour without heating and filtered and the residue is washed with 350 ml of water and 150 ml of methanol. After drying, 2.74 g (97%) of luminous yellow crystals of the formula (XX)

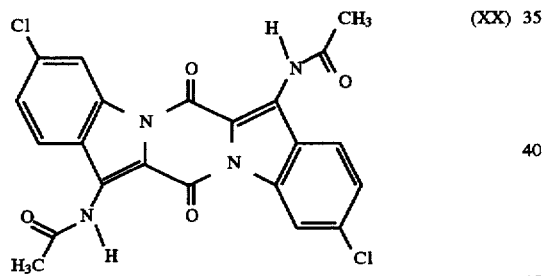

(XX)

and the elemental composition: C 56.10%, H 3.02%, N 11.89%, Cl 15.16%

(calculated for $C_{22}H_{14}N_4O_4Cl_2$: C 56.31%, H 3.01%, N 11.94%, Cl 15.11%)

are obtained.

EXAMPLE 7

1.26 g of the compound of the formula (XXI)

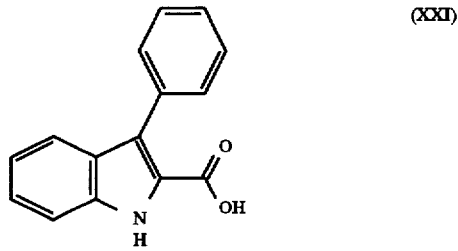

(XXI)

(prepared according to Beilstein E II 22, 68) are dissolved in 10 ml of methylene chloride and the solution is stirred at room temperature and under an inert gas for 4 hours, with the addition of 0.76 g of thionyl chloride. The solvent and the excess $SOCl_2$ are stripped off. The residue is dissolved in 10 ml of methylene chloride, and 1.0 g of pyridine is added. The reaction mixture is stirred at room temperature for 14 hours. A yellow precipitate is obtained by this procedure and is filtered over a hard paper filter and washed with a further 10 ml of methylene chloride. The yellow powder is after-treated in 20 ml of boiling diacetone alcohol for 14 hours. 1.0 g (86% of theory) of a yellow product of the formula (XXII)

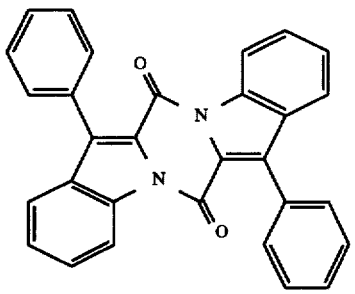

(XXII)

and the elemental composition: C 80.95%, H 4.13%, N 6.22%

(calculated for $C_{30}H_{18}N_2O_2$: C 82.18%, H 4.14%, N 6.39%)

is obtained.

EXAMPLE 8

3.70 g of the compound of the formula (XIV) from Example 4 and 2.94 g of thiobarbituric acid are suspended in 150 ml of DMF. 5 ml of triethyl orthoformate are stirred into the pale brown suspension and the reaction mixture is heated up to 115° C., the ethanol liberated during the reaction being distilled off. The now orange suspension is stirred at 115° C. for a further 20 hours and filtered and the residue is washed with 100 ml of methanol. The still somewhat moist press-cake is taken up in 150 ml of DMA and the mixture is stirred at 120° C. for 20 hours. The suspension is cooled to room temperature and filtered and the residue is washed with 240 ml of methanol and 300 ml of water and dried. 5.75 g (85% of theory) of an orange-coloured powder of the formula (XXIII)

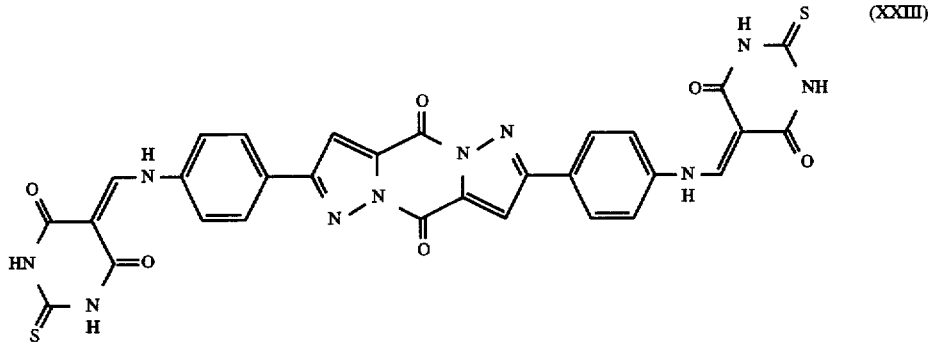

(XXIII)

and the elemental composition: C 51.28%, H 3.12%, N 19.90%, S 8.02%

(calculated for $C_{30}H_{18}N_{10}O_6S_2 \cdot 1.4H_2O$: C 51.19%, H 2.98%, N 19.90%, S are obtained.

EXAMPLES 9–24

In each case 1 part by weight of the stated compound from the stated incorporated into 100 parts by weight of the stated polymer. Brilliant colorations ed colour with the stated fastnesses are obtained (PVC=polyvinyl chloride, HDPE= high density polyethylene):

| Example No. | Compound of the formula | from Example | Polymer | Colour obtained | Fastnesses obtained |
|---|---|---|---|---|---|
| 9 | (VIII) | 1 | PVC | orange-yellow | very good |
| 10 | (VIII) | 1 | HDPE | orange-yellow | very good |
| 11 | (IX) | 2 | PVC | yellow-orange[‡,†] | good |
| 12 | (IX) | 2 | HDPE | yellow-orange[†,‡] | good |
| 13 | (XI) | 3 | PVC | yellow[‡] | very good |
| 14 | (XI) | 3 | HDPE | yellow[‡] | very good |
| 15 | (XV) | 4 | PVC | yellow | very good |
| 16 | (XV) | 4 | HDPE | yellow | very good |
| 17 | (XVII) | 5 | PVC | orange | very good |
| 18 | (XVII) | 5 | HDPE | orange | very good |
| 19 | (XX) | 6 | PVC | greenish-tinged yellow[†] | good |
| 20 | (XX) | 6 | HDPE | greenish-tinged yellow[†] | good |
| 21 | (XXII) | 7 | PVC | greenish-tinged yellow | good |
| 22 | (XXII) | 7 | HDPE | greenish-tinged yellow | good |
| 23 | (XXIII) | 8 | PVC | yellow | good |
| 24 | (XXIII) | 8 | HDPE | yellow | good |

[†] these colorations are distinguished by a particularly high brilliance
[‡] these colorations are distinguished by a particularly good tinctorial strength

What is claimed is:

1. A process for bulk coloration of high molecular weight organic material, which comprises incorporating into said high molecular weight organic material a tinctorially effective amount of a compound of the formula (I)

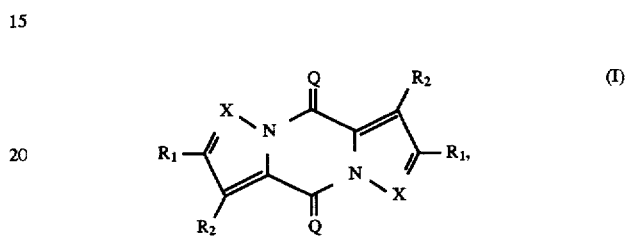

(I)

in which Q is O or S, and

X is $C(R_3)$ or N.

$R_1$, $R_2$ and $R_3$ independently of one another are hydrogen, chlorine, bromine, fluorine, $C_1$–$C_6$alkyl, $C_1$–$C_6$alkoxy, hydroxyl, cyano, nitro, amino, morpholino,

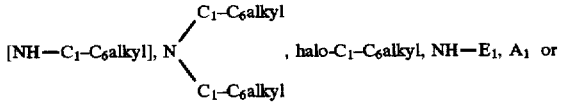

, halo-$C_1$–$C_6$alkyl, NH—$E_1$, $A_1$ or $N\begin{smallmatrix}A_2\\E_1\end{smallmatrix}$, in which $A_1$ and $A_2$ independently of one another are $C_6$–$C_{12}$aryl substituted by 3 radicals $R_4$, $R_5$ and $R_6$, or $C_3$–$C_{12}$heteroaryl which is substituted by 3 radicals $R_4$, $R_5$ and $R_6$ and contains, in the ring system, 1 to 3 hetero atoms chosen from the group consisting of N, O and S, and $E_1$

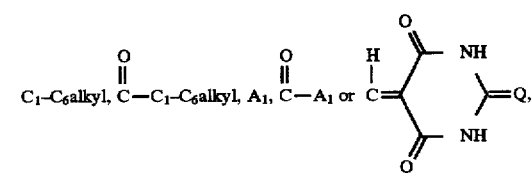

or $R_1$ and $R_2$ together, or $R_1$ and $R_3$ together, are a radical $A_3$, which $A_3$ is $C_4$–$C_8$alkenylene or $C_8$–$C_{12}$aralkenylene which are substituted by 3 radicals $R_7$, $R_8$ and $R_9$, and $R_4$ to $R_9$ independently of one another are hydrogen, chlorine, bromine fluorine, $C_1$–$C_6$alkyl, $C_1$–$C_6$alkoxy, hydroxyl, cyano, nitro, amino, morpholino,

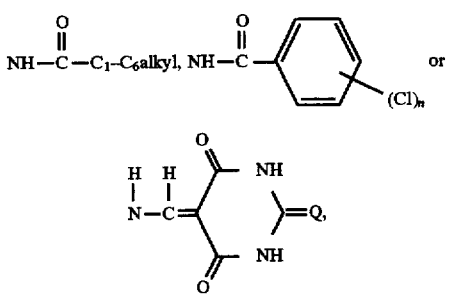

in which n is zero or an integer from 1 to 3.

2. A process according to claim 1, wherein, in formula (I), Q is O.

3. A process according to claim 1, wherein X is N and $R_1$ and $R_2$ are $C_1$–$C_4$alkyl, $C_1$–$C_4$alkoxy, amino, $A_1$ or NH—$E_1$.

4. A process according to claim 3, wherein $A_1$ is $C_6$–$C_{12}$aryl substituted by 3 radicals $R_{10}$, $R_{11}$ and $R_{12}$, in which $R_{10}$ to $R_{12}$ independently of one another are $R_4$ to $R_6$.

5. A process according to claim 4, wherein $R_{10}$ to $R_{12}$ are hydrogen, $C_1$–$C_6$alkoxy, amino,

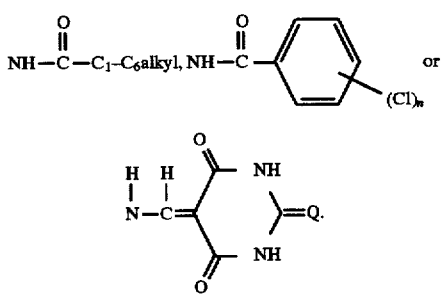

6. A process according to claim 1, wherein X is $C(R_3)$, one radical $R_1$ or $R_2$ is $C_1$–$C_4$alkyl, $C_1$–$C_4$alkoxy, amino, $A_1$ or NH—$E_1$, and the other radical $R_2$ or $R_1$ together with $R_3$ forms a radical

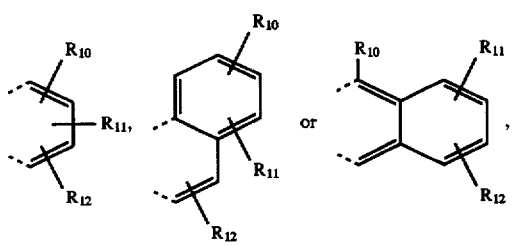

in which $R_{10}$ to $R_{12}$ independently of one another are hydrogen, chlorine, bromine, fluorine, $C_1$–$C_6$alkyl, $C_1$–$C_6$alkoxy hydroxyl, cyano, nitro, amino, morpholino,

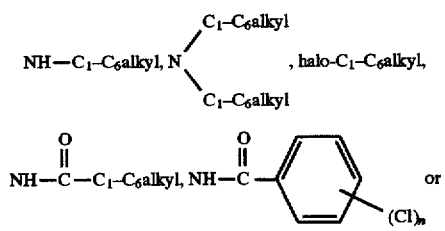

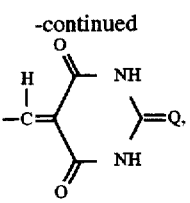

in which n is zero or an integer from 1 to 3.

7. A process according to claim 6, in which $R_1$, together with $R_3$, forms a radical

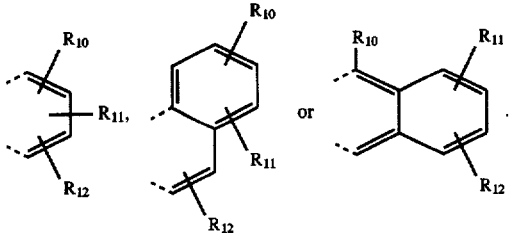

8. A process according to claim 1, wherein the compound of the formula (I) has at least two hydrogens each bonded to a nitrogen in at least one tautomeric form.

9. A process according to claim 1, wherein the compound of the formula (I) has a specific BET surface area of 5–150 m²/g.

10. A process according to claim 1, wherein the compound of the formula (I) is employed in an amount of 0.01 to 30% by weight, based on the high molecular weight organic material to be coloured.

11. A process according to claim 1, wherein

1) X is N, $R_1$ is methyl, ethyl or $A_1$ and $R_2$ is amino or NH—$E_1$;

2) X is N, $R_1$ is a radical $A_1$ and $R_2$ is hydrogen;

3) X is N, $R_1$ is hydrogen and $R_2$ is amino, morpholino,

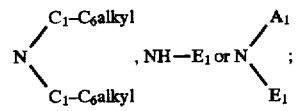

or

4) X is $C(R_{13})$, $R_1$ and $R_2$ together are a radical

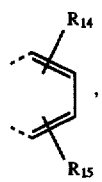

$R_{13}$ is amino or NH—$E_1$ and $R_{14}$ and $R_{15}$ independently of one another are hydrogen, amino, NH—$E_1$ or nitro.

12. A process according to claim 10, wherein the compound of the formula (I) is employed in an amount of 0.1 to 10% by weight, based on the high molecular weight organic material to be colored.

13. A compound of the formula (IV), (V) or (VI),

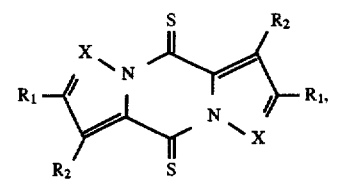  (IV)

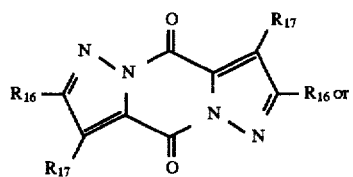  (V)

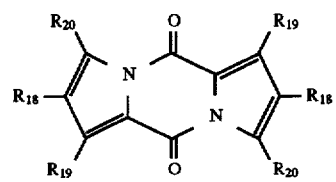  (VI)

wherein X is C(R$_3$) or N, and R$_1$, R$_2$ and R$_3$ independently of one another hydrogen, chlorine, bromine, fluorine, C$_1$–C$_6$alkoxy, hydroxy, cyano, nitro, amino, morpholino,

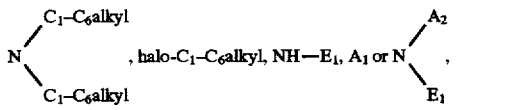

in which A$_1$ and A$_2$ independently of one another are C$_6$–C$_{12}$aryl substituted by 3 radicals R$_4$, R$_5$ and R$_6$, or C$_3$–C$_{12}$ heteroaryl which is substituted by 3 radicals R$_4$, R$_5$ and R$_6$ and contains, in the ring system, 1 to 3 hetero atoms chosen from the group consisting of N, O and S, and E$_1$ is

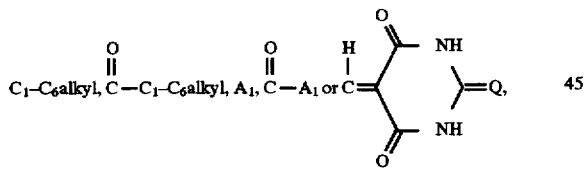

or R$_1$ and R$_2$ together are a radical A$_3$,
which A$_3$ is C$_4$–C$_8$alkenylene or C$_8$–C$_{12}$aralkenylene which are substituted by 3 radicals R$_7$, R$_8$ and R$_9$,
and R$_4$ to R$_9$ independently of one another are hydrogen, chlorine, bromine, fluorine, C$_1$–C$_6$alkyl, C$_1$–C$_6$alkoxy, hydroxyl, cyano, nitro, amino, morpholino,

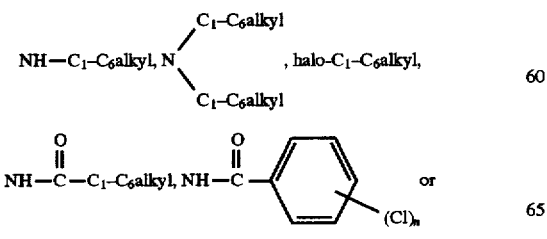

-continued

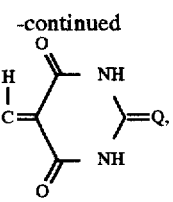

in which n is zero or an integer from 1 to 3;

R$_{16}$ and R$_{17}$ independently of one another are hydrogen, chlorine, bromine fluorine, C$_1$–C$_6$alkyl, C$_1$–C$_6$alkoxy, hydroxyl, cyano, nitro, amino, morpholino,

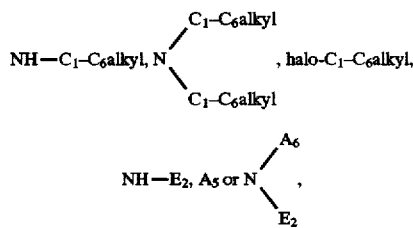

in which A$_5$ and A$_6$ independently of one another are C$_6$–C$_{12}$aryl substituted by 3 radicals R$_{21}$, R$_{22}$ and R$_{23}$, or C$_3$–C$_{12}$heteroaryl which is substituted by 3 radicals R$_{21}$, R$_{22}$ and R$_{23}$ and contains, in the ring system, 1 to 3 hetero atoms chosen from the group consisting of N, O and S, and E$_2$ is

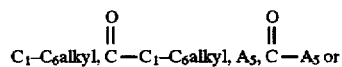

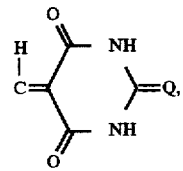

with the proviso that either R$_{16}$ is C$_6$–C$_{12}$aryl substituted by at least one radical of the group consisting of C$_1$–C$_6$alkoxy, amino, morpholino,

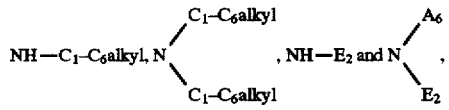

or R$_{17}$ is C$_1$–C$_6$alkoxy, amino, morpholino,

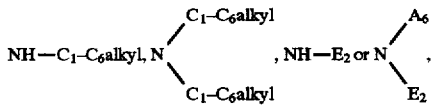

or, if R$_{16}$ is not hydrogen, is A$_5$,
or R$_{16}$ and R$_{17}$ together are a radical A$_7$, in which
A$_7$ is C$_4$–C$_8$alkenylene or C$_8$–C$_{12}$arylene which are substituted by 3 radicals R$_{24}$, R$_{25}$ and R$_{26}$, with the proviso that A$_7$ is substituted by at least one radical C$_1$–C$_6$alkoxy;

R$_{18}$, R$_{19}$ and R$_{20}$ independently of one another are hydrogen, chlorine, bromine fluorine, C$_1$–C$_6$alkyl, $C_1$–$C_6$alkoxy, hydroxyl, cyano, nitro, amino, morpholino,

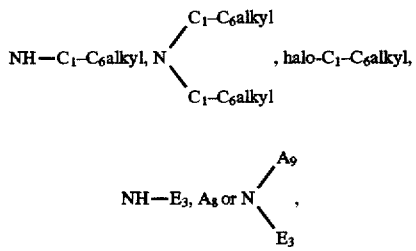

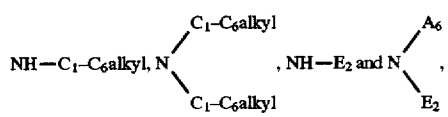

in which $A_8$ and $A_9$ independently of one another are $C_6$–$C_{12}$aryl substituted by 3 radicals $R_{21}$, $R_{22}$ and $R_{23}$, or $C_3$–$C_{12}$heteroaryl which is substituted by 3 radicals $R_{21}$, $R_{22}$ and $R_{23}$ and contains, the ring system, 1 to 3 hetero atoms chosen from the group consisting of N, O and S, and $E_3$

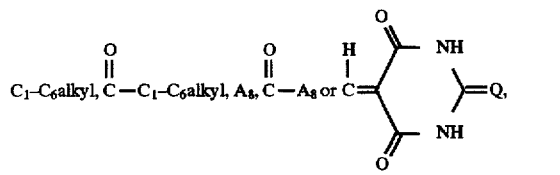

with the proviso that either $R_{19}$ is $C_1$–$C_6$alkoxy, amino, morpholino,

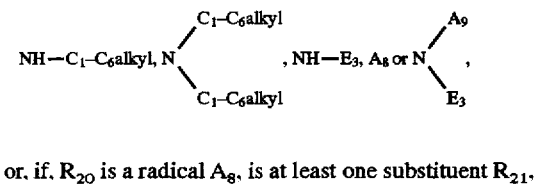

or, if, $R_{20}$ is a radical $A_8$, is at least one substituent $R_{21}$, or $R_{18}$ is $C_1$–$C_6$alkoxy, morpholino,

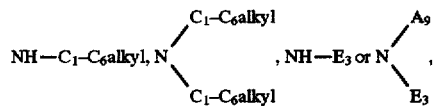

or, if $R_{19}$ and $R_{20}$ are not hydrogen, is amino, or $R_{18}$ and $R_{19}$ together are a radical $A_{10}$, which $A_{10}$ is $C_4$–$C_8$alkenylene or $C_8$–$C_{12}$arylene substituted by 3 radicals $R_{24}$, $R_{25}$ and $R_{26}$, with the proviso that $A_{10}$ is substituted by at least one radical from the group consisting of $C_1$–$C_6$alkoxy, amino, morpholino, or $R_{18}$ and $R_{20}$ together are a radical $A_{11}$, which $A_{11}$ is $C_4$–$C_8$alkenylene or $C_8$–$C_{12}$arylene which are substituted by 3 radicals $R_{24}$, $R_{25}$ $R_{26}$, with the proviso that, if $R_{18}$ and $R_{20}$ together are a radical $A_{11}$, $R_{19}$ is other than hydrogen, and, if $R_{19}$ is amino, hydroxy, cyano, phenyl, 2-fluoro-phenyl, 2-chlorophenyl or $C_1$–$C_6$alkyl, $A_{11}$ is substituted by at least one radical from the group consisting of $C_1$–$C_6$alkoxy, amino, morpholino,

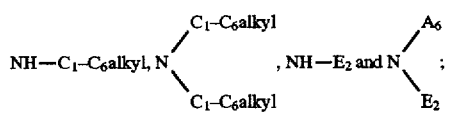

in which $R_{21}$ to $R_{26}$ independently of one another are hydrogen, chlorine, bromine fluorine, $C_1$–$C_6$alkyl, $C_1$–$C_6$alkoxy, hydroxyl, cyano, nitro, amino, morpholino,

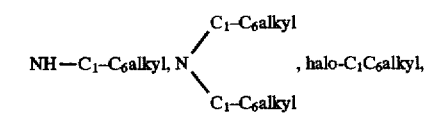

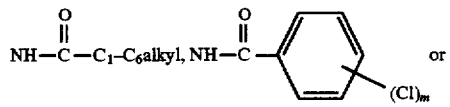

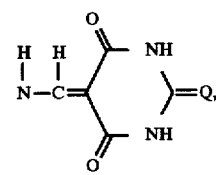

in which m is zero or an integer from 1 to 3; and Q is O or S.

14. A compound according to claim 13, which contains at least one group from the series consisting of $C_1$–$C_6$alkoxy, amino, morpholino,

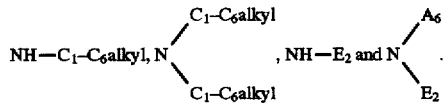

15. A composition of substances comprising a compound of the formula (I) according to claim 1 and a high molecular weight organic material.

* * * * *